United States Patent [19]

Kurtz

[11] Patent Number: 4,875,896
[45] Date of Patent: Oct. 24, 1989

[54] NEEDLE DISPOSAL DEVICE AND METHOD FOR PREVENTING ACCIDENTAL CONTACT WITH A NEEDLE

[76] Inventor: Sharon L. Kurtz, 335 Ballantrae La., Houston, Tex. 77015

[21] Appl. No.: 237,326

[22] Filed: Aug. 29, 1988

[51] Int. Cl.⁴ ............................................... A61M 5/00
[52] U.S. Cl. ........................... 604/187; 128/DIG. 26; 206/365
[58] Field of Search ............... 604/187, 162, 163, 180; 206/63.3, 364, 365, 484, 484.1, 524.2, 813; 128/DIG. 26

[56] References Cited

U.S. PATENT DOCUMENTS 4,758,229 7/1988 Doerschner .................... 604/187

Primary Examiner—John D. Yasko
Attorney, Agent, or Firm—Ben D. Tobor

[57] ABSTRACT

A needle disposal device and method comprising at least two planar members connected together along a side edge. Adhesive material on the surface of one of the planar members for contacting a needle and second securing means securing together the front surfaces of the planar members when moved together to fixedly sandwich the needle between the planar members.

28 Claims, 2 Drawing Sheets

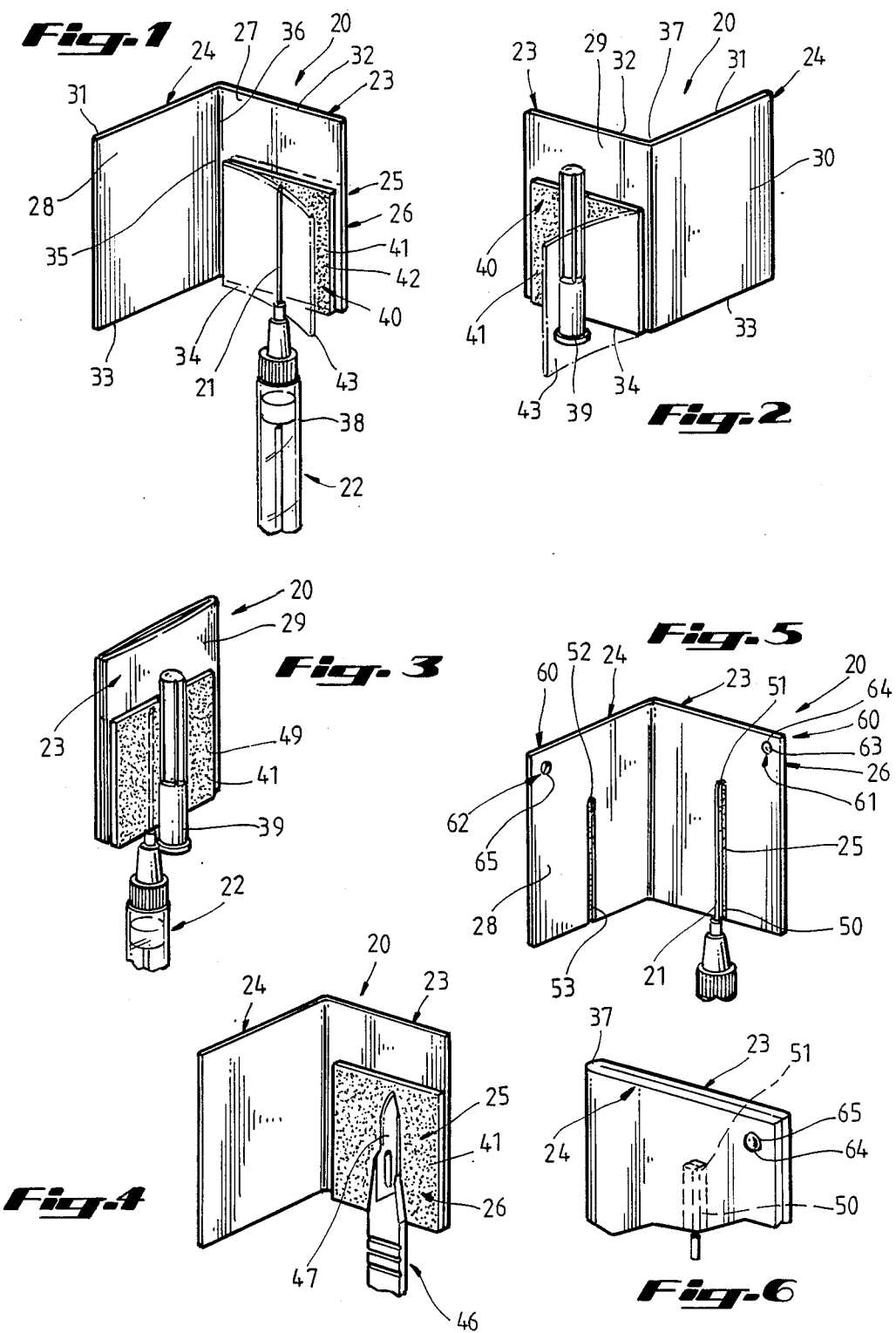

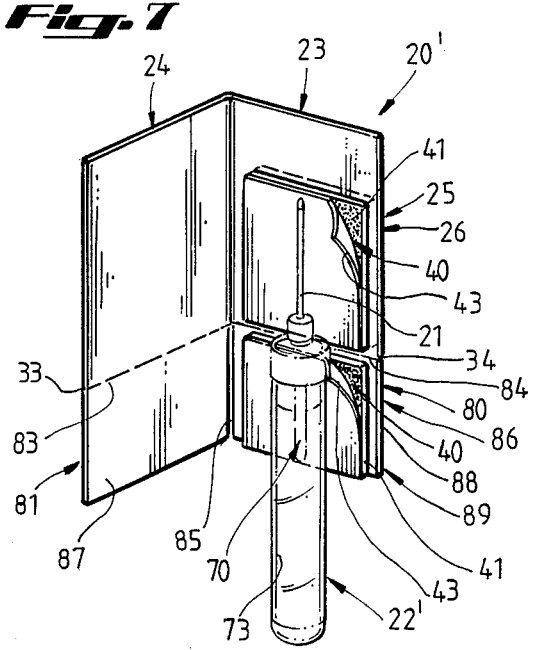
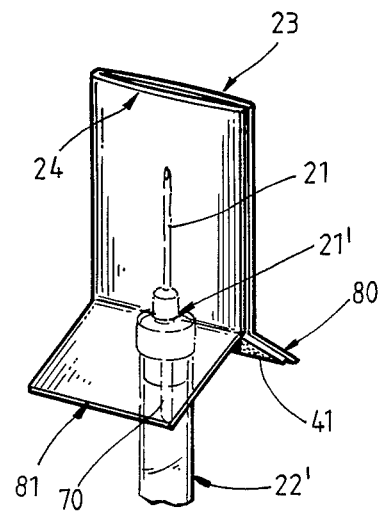
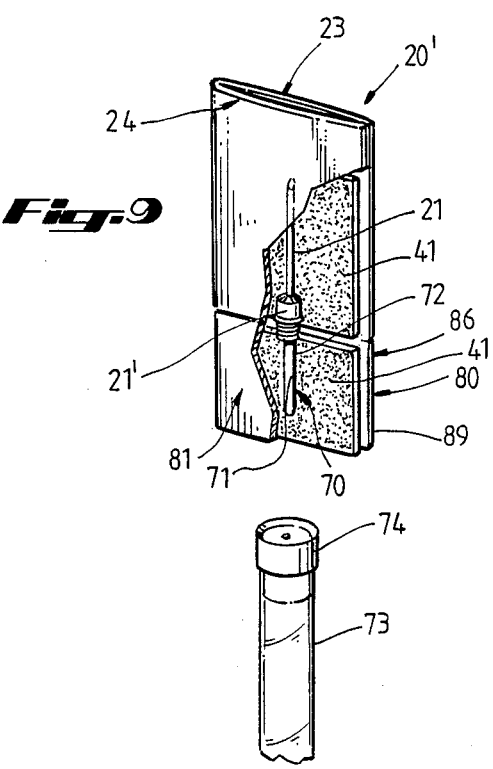
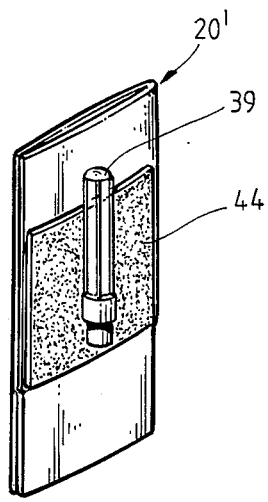

NEEDLE DISPOSAL DEVICE AND METHOD FOR PREVENTING ACCIDENTAL CONTACT WITH A NEEDLE

BACKGROUND OF THE INVENTION

1. Field of the Invention

The invention relates to a disposal device for needles, such as for hypodermic syringes, disposable scalpels, and a method for preventing accidental contact with the needle of a hypodermic syringe after the needle has been used.

2. Description of the Prior Art

As is conventional in the art, a hypodermic syringe is used to inject substances into human and animal bodies. A typical hypodermic syringe comprises: a barrel, adapted to contain the substance to be injected; a hypodermic needle, or sharp-pointed cannula, coupled to the barrel; and means for forcing, such as a plunger, the substance from the barrel through the needle or cannula.

Hypodermic syringes are typically disposable and are discarded after use. One problem presented by the disposal of the syringes is in shielding the sharp end of the needle, or cannula, so that those handling it will not be stuck or accidentally pricked. This problem is particularly important because, following the injection, the needle may be contaminated from its exposure to the human or animal blood and can spread diseases, such as hepatitis or AIDS.

Typically, hypodermic syringes are supplied with a tubular shield which is slipped over the pointed end of the needle and releasably retained on the syringe as by a frictional fit with a mounting post formed on the end of the syringe barrel. The most conventional method to shield the needle following its use is to replace the tubular shield. Unfortunately, however, the passage into the shield is of small diameter and the shield must be inserted over the sharp end of the needle. Consequently, there is a substantial risk to the person attempting to do this, particularly if the reshielding is attempted during emergency periods or other times of high stress, such as in emergency operating rooms, at the scene of an accident, or in a moving ambulance.

An additional problem associated with conventional hypodermic syringes is that in many instances, particularly in emergency-type situations, the syringe will be used and laid down somewhere in the operating room, without the syringe having been resheathed. Thus, the opportunity also exists that individuals in the operating room, or other emergency scene, could walk by and accidentally contact a potentially contaminated needle.

One proposed solution to the foregoing problems has been to incorporate a slideable exterior sheath about the barrel of the hypodermic syringe, whereby after the syringe has been used, the sheath is moved along the barrel until it resheaths the used needle. Examples of such hypodermic syringes are found in U.S. Pat. Nos. 4,702,738; 4,026,287; and 4,425,120. It is believed that syringe manufacturers have not adopted such hypodermic syringes because of the additional cost involved in providing the slideable sheath, and perhaps problems associated with molding the additional components. Furthermore, since each manufacturer of syringes utilizes a different design, as well as manufactures syringes in a multitude of different sizes and shapes, a large number of manufacturing modifications, including additional molds, would have to be accomplished prior to providing such type of protection to the hypodermic syringes.

Presently, some syringe manufacturers have advised the users of their products to dispose used syringes into a metal, or heavy cardboard, box, without resheathing the needle. There are problems associated with this suggested method for disposing of used syringes. Since the box may be ultimately emptied, the risk of accidental contact with the used needles is greatly increased, insofar as none of the needles have been resheathed. An additional problem associated with this suggested method is that its practice would likely increase the opportunity for accidental contact with a used needle, in that medical personnel would have to walk through an operating room, or emergency room, with an unsheathed needle, in order to get to where the metal disposal box is located, rather than resheath it immediately after its use.

Accordingly, prior to the development of the present invention, there has been no disposal device for needles or method for preventing accidental contact with a needle which: is simple and economical to manufacture; is easily used; has universal application for any needle or other sharp medical device; and helps to prevent accidental contact with a used needle. Therefore, the art has sought a disposal device for needles and method for preventing accidental contact with a needle which: is simple and economical to manufacture; is easily used; has universal application for any needle or other sharp medical device; and helps to prevent accidental contact with a needle of a hypodermic syringe after the needle has been used.

SUMMARY OF THE INVENTION

In accordance with the invention, the foregoing advantages have been achieved through the present disposal device for a needle which is adapted for use in a hypodermic syringe. The present invention includes: at least two planar members, each planar member having front and back surfaces, and top edge, bottom edge, and side edge surfaces; the two planar members being flexibly connected together along a side edge surface of each planar member; first means for securing the needle to the front surface of one the planar members; and second means for securing together the front surfaces of the planar members upon one of the planar members being moved into contact with the other planar member, whereby the needle may be first associated with the first securing means, and a planar member is then moved to engage the second securing means to fixedly sandwich the needle between the planar members. The first securing means may comprise an adhesive material disposed on the front surface of one of the planar members, and the second securing means may be a portion of the same adhesive material that forms the first securing means.

Another feature of the present invention is that the second securing means may be a connector mechanism having cooperating elements disposed on both planar members. A further feature of the present invention is that the first securing means may include an indentation formed in at least one front surface of a planar member, the indentation forming a cavity adapted for receipt of the needle.

In accordance with the invention, the foregoing advantages may also be achieved through a disposal device including four planar members, each planar member having front and back surfaces, and top edge, bottom edge, and side edge surfaces; two of the planar members being flexibly connected together along a side edge surface of each of the two planar members to form a first connected pair of planar members: each of the other two planar members being flexibly connected along its top edge surface to the bottom edge surface of one of the planar members of the first connected pair of planar members; first means for securing a first portion of the needle to the front surface of one of the planar members of the first connected pair of planar members; second means for securing together the front surfaces of the first connected pair of planar members, upon one of planar members of the first connected pair being moved into contact with the other planar member of the first connected pair; third means for securing together the front surfaces of the other two planar members upon the movement of one of the other planar members toward one of the other planar members, whereby the first portion of the needle may be first associated with the first securing means, one of planar members of the first connected pair of planar members is moved to engage the second securing means to fixedly sandwich the first portion of the needle between the first connected pair of planar members, and the other two planar members are moved toward each other until one of them engages the third securing means. Another feature of the present invention is that a fourth means for securing a second portion of the needle, which downwardly depends from the first portion of the needle, to the second surface of one of the other planar members may be provided.

In accordance with the invention, the foregoing advantages have also been achieved through the present method for preventing accidental contact with a needle of a hypodermic syringe after the needle has been used. The present invention includes the steps of: associating the needle with a first planar member; securing the needle to the planar member; and securing a second planar member to the first planar member with the needle disposed between the two planar members. A feature of the present invention is that the needle may be associated with the first planar member by laying the needle upon the first planar member. Another feature of the present invention is that the needle may be secured to the first planar member by the member contacting an adhesive material disposed upon the first planar member. Another feature of the present invention is that the second planar member may be secured to the first planar member by an adhesive material disposed upon the first planar member. A further feature of the present invention is that the second planar member may be secured to the first planar member by a connector mechanism having cooperating elements on both of the planar members.

The disposal device and method for preventing accidental contact with a needle of a hypodermic syringe after the needle has been used of the present invention, when compared with previously proposed prior art disposal devices and methods, has the advantages of: universal application for any type of syringe; ability to dispose of dual-type needles; being economical to manufacture; easily used; ability to be used to dispose of disposable scalpels and other types of disposable medical instruments; and helping to prevent accidental contact with a needle of a hypodermic syringe after the needle has been used.

BRIEF DESCRIPTION OF THE DRAWINGS

FIG. 1 is a front perspective view of a disposal device in accordance with the present invention;

FIG. 2 is a rear perspective view of a disposal device in accordance with the present invention;

FIG. 3 is a perspective view of a disposal device in accordance with the present invention with the needle being ready to be discarded;

FIG. 4 is a front perspective view of a disposal device in accordance with the present invention, wherein a disposable scalpel is being used with the disposal device.

FIG. 5 is a front perspective view of another disposal device in accordance with the present invention:

FIG. 6 is a partial perspective view of the disposal device of FIG. 5;

FIG. 7 is a front perspective view of another disposal device in accordance with the present invention;

FIG. 8 is a perspective view of the disposal device of FIG. 7;

FIG. 9 is a perspective view of the disposal device of FIG. 7 which is ready to be disposed of; and FIG. 10 is a perspective view of the rear of the disposal device of FIG. 9.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIG. 1, a disposal device 20 for a needle, or cannula. 21 for use in a hypodermic syringe 22, in accordance with the present invention, is shown to comprise at least two planar members 23,24; a first means for securing 25 the needle 21 to one of the planar members 23,24; and a second means 26 for securing together the planar members 23,24 upon one of the planar members 23,24 being moved into contact with the other planar member, whereby the needle 21 may be first associated with the first securing means 25, and a planar member 24 is then moved to engage the second securing means 26 to fixedly sandwich the needle 21 between the planar members 23,24. It should be noted, as will become readily apparent to one skilled in the art, that disposal device 20 may also be used for a variety of other sharp medical devices used by medical personnel, such as butterfly needles, phlebotomy needles, blood transfusion needles, disposable scalpels, and disposable scalpel blades.

With reference to FIGS. 1 and 2, it is seen that each planar member 23.24 has front surfaces 27,28, back surfaces 29,30, top edge surfaces 31,32, bottom edge surfaces 33,34, and side edge surfaces 35,36. As seen in FIGS. 1-3, the two planar members 23,24 are flexibly connected together along a side edge surface 35,36, of each planar member 23,24. Planar members 23,24, may be formed of any suitable material having the requisite strength characteristics to withstand a slight accidental piercing contact with needle 21, such as cardboard, wood, metal, or a plastic material. Preferably, planar members 23,24 are made from a suitable plastic material such as polyethylene sheet material. Planar members 23,24 may be flexibly connected together along the side edge surfaces 35,36 in any convenient manner, such as by taping the two planar members together, providing a hinge 37 (FIG. 6) molded integrally between planar member 23,24, or by forming planar members 23,24 from one sheet of material which is then scored to form side edge surfaces 35,36, whereby planar members 23,24 may be bent about the score line. Although throughout the drawings, planar members 23,24 are illustrated to generally have a square or rectangular shape, as will be hereinafter apparent, planar members 23,24 could have other geometric configurations. As to size, it is preferred that each planar member 23,24 be the same size, and the only size consideration is that the length of needle 21 be less than the distance between the top and bottom edges of the planar members 23,24. As will hereinafter become apparent, disposal device 20 could also be utilized to dispose of a needle 21 if needle 21 and syringe 22 are rotated, from their positions shown in FIG. 1, about an angle of 90 degrees with respect to the disposal device 20. Syringe 22 may be of any construction, including permitting the removal of needle 21 from the barrel 38 of syringe 22, such as by rotating barrel 38 with respect to needle 21, or needle 21 may be fixedly secured to barrel 38 of syringe 22. Syringe 22, as is conventional in the art, is initially provided with a removable tubular shield, or sheath 39, which is shown in FIGS. 2 and 3, as will be hereinafter described in further detail.

Still with reference to FIG. 1, the first means for securing 25 the needle 21 to the front surface 27 of one of the planar members 23 may comprise an adhesive material 40 disposed on the front surface 27 of one of the planar members, such as planar member 23. Adhesive material 40 may be a layer of any suitable adhesive material, such as glue, transparent polyester tape, or any suitable tacky surface which can exert a sufficient adhesive force upon needle 21 to secure it to planar member 23. Preferably, adhesive material 40 is a layer of conventional foam adhesive tape 41, which typically has an adhesion surface on its front and back, one of the adhesion surfaces 42 being provided with a removable protective layer 43, which may be readily removed prior to the needle 21 being associated with the adhesive material 40 as will be hereinafter described in greater detail. The second means for securing 26 together the front surfaces 27,28 of planar members 23,24 upon one of the planar members 23,24 being moved into contact with the other planar member, may comprise a portion of the same adhesive material 40 that forms the first securing means 25. For example, that portion of foam tape 41 which does not contact needle 21 is available to contact the front surface 28 of planar member 24 upon planar member 24 being moved into engagement with foam tape 41. As seen in FIGS. 2 and 3, the back surface 29 of one of the planar members, such as planar member 23, may be provided with an adhesive mounting surface 44 which is adapted to hold the tubular shield, or sheath, 39 which is initially associated with syringe 22. Adhesive mounting surface 44 is preferably another layer of foam adhesive tape 41, which is also provided with a protective layer 43 as shown in FIG. 2.

With reference to FIGS. 1-3, the operation of disposal device 20 will be described. It is envisioned that disposal device 20 will be used in the following manner, however, it is possible that slight modifications in the manner of use could occur. At the time that an individual selects a syringe 22, including needle 21 and sheath 39 for use with a patient, the individual would also obtain a disposal device 20. The individual would remove protective layer 43 from adhesive mounting surface 44 disposed on the back surface 29 of one of the planar members, such as planar member 23, and sheath 39 with needle 21 therein along with barrel 38 of syringe 22, would be pressed upon adhesive mounting surface 44. Sheath 39 would thus be fixedly secured to disposal device 20. The needle 21 and barrel 38 of syringe 22 may then be removed from sheath 39 and syringe 22 would be filled in a conventional manner. The syringe could then be used to give an injection in a conventional manner, or syringe 22 could be resheathed by inserting needle 21 of syringe 22 back into the sheath 39 which is secured to disposal device 20. Although it is possible that the individual could accidentally be pricked by needle 21, such accidental contact would likely not cause any harm to that individual, insofar as the needle has not as of yet been used to give an injection, and it is therefore not contaminated. After the injection has been given, or prior to the injection having been given, the protective layer 43 is removed from the foam tape 41 which is disposed on the front surface 27 of planar member 23. After the injection has been given, the individual holding the syringe 22 would then associate needle 21 with the first securing means 25, or foam tape 41, such as by laying needle 21 upon foam tape 41. It is believed that there is much less opportunity for the individual to accidentally prick themselves with needle 21 when the needle is being laid upon foam tape 41, than the opportunity typically encountered when trying to conventionally insert a used needle 21 into sheath 39. Upon needle 21 being secured to the front surface 27 of planar member 23, planar member 24 is moved to engage the second securing means 26 to fixedly sandwich the needle 21 between the planar members 23,24, as shown in FIG. 3. If needle 21 is removable from the barrel 38 of syringe 22, at that time barrel 38 can be rotated with respect to needle 21, whereby needle 21 will become disengaged from barrel 38. In any event, as seen in FIG. 3, the potentially contaminated needle 21, as seen in FIG. 3, cannot accidentally come into contact with an individual handling disposal device 20. As should be readily apparent to one of ordinary skill in the art, it is not necessary to utilize the adhesive mounting surface 44 to hold sheath 39 in the manner previously described, in that such a step can be optional.

With reference to FIG. 4, it is seen that disposal device 20 of FIGS. 1-3 may likewise be utilized with a conventional disposable scalpel 46, having a blade 47 thereon, which is secured by the first securing means 25 in the same manner as needle 21 as discussed in connection with FIGS. 1-3. Likewise, the second securing means 26 as previously described would secure planar member 24 to planar member 23, whereby accidental contact with a used scalpel 46 is also prevented.

With reference to FIGS. 5 and 6, different forms of securing means 25,26 are illustrated. The same reference numerals are used throughout all of the figures to describe identical components of disposal device 20. As seen in FIGS. 5 and 6, the first securing means 25 may include an indentation 50 formed in at least one front surface, such as front surface 27 of planar member 23, whereby the indentation 50 forms a cavity 51 adapted for receipt of the needle 21. As seen in FIG. 5, another mating indentation 52, which forms a cavity 53 may be provided in the front surface 28 of the other planar member 24. At least one cavity. 51, may be provided with a suitable adhesive material 54 therein. Adhesive material 54 could be a strip of foam tape, such as that shown at 41 in FIG. 1, or adhesive material 54 could be any suitable glue, whereby upon needle 21 being laid within indentation 50, needle 21 would be secured to the front surface 27 of planar member 23 in a similar manner as that previously described in connection with disposal device 20 illustrated in FIGS. 1-3. Second securing means 26 is a connector mechanism 60 having cooperating elements 61,62 disposed on both planar members 23,24. As illustrated in FIG. 5, connector mechanism 60 can be a pin member 63 with an enlarged end 64 (FIG. 6) which is engageable with a mating opening 65 formed in the other planar member 24. Accordingly, upon the two planar members 23,24 being pressed together, the enlarged head 64 of pin member 63 passes through opening 65 and secures the two planar members together. Alternatively, any other type of a suitable conventional connector mechanism, such as VELCRO ® material could be utilized. Additionally, the first securing means 25 illustrated in FIGS. 5-6 could be utilized with adhesive material 40, such as foam tape 41, for the second securing means 26, in lieu of the connector mechanism 60 illustrated in FIGS. 5-6. Indentations 50,52, can be formed within planar members 23,24, such as by molding them integrally within planar members 23,24, or by a separate material removing step, in a conventional manner.

With reference now to FIGS. 7-10, another embodiment of disposal device 20' in accordance with the present invention will be described. The same reference numerals will be utilized for components of disposal device 20' which have been previously described in connection with FIGS. 1-6. The disposal device 20' of FIGS. 7-10 is particularly useful for use with needles 21' (FIG. 9) which are used in connection with certain types of blood sampling equipment, such as that sold by Becton Dickinson, Inc. under the trademark VACU-TAINER ®. In these types of blood sampling equipment, a needle 21' has a conventional needle 21 as previously described, needle 21 forming a first portion of needle 21'. Depending downwardly from needle 21 of needle 21' is a second portion 70 of needle 21'. Second portion 70 is another needle 71 disposed within a flexible, elastic sheath 72, needle 71 being in fluid communication with needle 21. In use, needle 21' is received within a special syringe 22', whereby needle 21 extends outwardly of syringe 22', and needle 71 extends downwardly within the syringe 22', as seen in FIG. 7. Needle 21' may also be provided with a tubular sheath 39 as previously described in connection with syringe 22. In taking a blood sample, a sealed test tube 73 having an elastic stopper 74 sealing test tube 73 is placed within syringe 22. A vacuum is present within the sealed test tube 73. Upon needle 71 puncturing seal 74, the vacuum within test tube 73 draws blood through needle 21 and through needle 71 and into test tube 73. After the desired blood samples have been taken, it is necessary to dispose of needle 21'.

As seen in FIG. 7, disposal device 20' includes four planar members 23,24,80,81. Planar members 23,24 are flexibly connected in the same manner as previously described in connection with disposal device 20 of FIGS. 1-6, and form a first connected pair 82 of planar members. The first connected pair of planar members 82 includes a first securing means 25 of the type as previously described in connection with FIGS. 1-6. The first connected pair of planar members 82 also includes a second securing means 26 of the same type as that previously described in connection with FIG. 1, although second connector means 26 could also be of the type as illustrated in FIGS. 5-6.

Still with reference to FIGS. 7-8, each of the other two planar members 80,81 is flexibly connected along its top edge surfaces 83,84 to the bottom edge surfaces 33,34, of the first connected pair of planar members 82. The flexible connection between planar members 81,24 and the flexible connection between planar members 80,23, may be provided in the same manner as the flexible connection between planar members 23,24 as previously described in connection with FIGS. 1-6. As seen in FIG. 7, planar members 80-81 are not connected to one another, in that a small gap 85 is present between planar members 80,81. A third means for securing together 86 the front surfaces 87,88 of the other planar members 80,81 is provided on the front surface 88 of planar member 80. Preferably, the third securing means 86 comprises an adhesive material 40, such as foam tape 41 as previously described in connection with the first and second securing means 25,26, of FIGS. 1-2. Additionally, a fourth means for securing the second portion of needle 21' may be provided to the front surface 88 of planar member 80. The fourth securing means 89 is also preferably an adhesive material 40, such as foam tape 41 as previously described in connection with FIGS. 1-3. It should be noted that third securing means 86 could be of the type as previously described in connection with FIGS. 5-6, such as connector mechanism 60. Likewise, the fourth securing means 89 could be of the type previously described in connection with FIGS. 5-6, such as indentations 50,52.

With reference now to FIG. 7-10, the operation of disposal device 20' will be described in greater detail. The steps for using disposal device 20' are identical with those previously described in connection with FIGS. 1-3, as to sandwiching the upper portion 21 of needle 21', whereby upon laying needle 21 upon the first securing means 25, and moving planar member 24 into engagement with second securing means 26, disposal device 20' will assume the configuration shown in FIG. 8, with the other planar members 80 and 81 being in the position shown in FIG. 8. When the device is in the configuration shown in FIG. 8, or prior thereto if desired, the protective layer 43 may be removed from foam tape 41, which is disposed upon planar member 80. After the downward removal of test tube 73, as illustrated in FIG. 9, the second portion of needle 21' or needle 71 and sheath 72 may then sandwiched between planar members 80,81, by moving planar members 80,81 into engagement with each other, whereby the third connector means 86 will secure connector members 80,81 to one another. Likewise, fourth securing means 89 will secure needle 71 and sheath 72 to planar member 80. As seen in FIG. 10, needle 21' is now contained within disposal device 20' and may be readily disposed of without fear of accidentally contacting an individual. As previously described in connection with disposal device 20 of FIGS. 1-3, the sheath 39 may be secured to adhesive mounting surface 44.

The method of preventing accidental contact with the needle 21 of a hypodermic syringe 22 after the needle 21 has been used, in accordance with the present invention, comprises the steps of associating: the needle 21 with the first planar member 23; securing the needle 21 to the planar member 23; and securing a second planar member, such as planar member 24, to the first planar member, such as planar member 23, with the needle 21 disposed between the two planar members 23,24. In connection with this method of the present invention, it is not necessary that the two planar members 23,24 be joined as illustrated in FIG. 1, although such construction is preferable. As previously described, the needle 21 may be associated with the first planar member 23, as by laying the needle 21 upon the first planar member 23.

It is to be understood that the invention is not limited to the exact details of construction, operation, exact materials, or embodiment shown and described, as obvious modifications and equivalents will be apparent to one skilled in the art: for example, the planar members could each be formed of a layer of foam tape. Accordingly, the invention is therefore to limited only by the scope of the appended claims.

I claim:

1. A disposal device for a needle which is adapted for use in a hypodermic syringe, or other sharp medical device, comprising:
    at least two planar members, each planar member having front and back surfaces, and top edge, bottom edge, and side edge surfaces and formed of a material able to withstand accidental piercing contact with the needle;
    the two planar members being fixedly connected together along a side edge surface of each planar member;
    first means for securing the needle to the front surface of one of the planar members wherein the first securing means is an adhesive material disposed on the front surface of one of the planar members and the needle contacts the adhesive material; and
    second means for securing together the front surfaces of the planar members upon one of the planar members being moved into contact with the other planar member, whereby the needle may be first associated with the first securing means, and a planar member is then moved to engage the second securing means to fixedly sandwiched the needle between the planar members.

2. The disposal device of claim 1, wherein the second securing means is a portion of the same adhesive material that forms the first securing means.

3. The disposal device of claim 1, wherein the second securing means is a connector mechanism having cooperating elements disposed on both planar members.

4. The disposal device of claim 1, wherein the adhesive material is a layer of foam adhesive tape.

5. The disposal device of claim 1, wherein the first securing means includes an indentation formed in at least one front surface of a planar member, the indentation forming a cavity adapted for receipt of the needle.

6. The disposal device of claim 5, wherein the second securing means is a connector mechanism having cooperating elements disposed on both planar members.

7. The disposal device of claim 5, wherein at least a portion of the cavity has an adhesive material therein.

8. The disposal device of claim 1, wherein a sheath is associated with the hypodermic syringe and, wherein the back surface of one of the planar members has an adhesive mounting surface adapted to hold the sheath.

9. The disposal device of claim 1, wherein the adhesive material is provided with a removable protective layer, which may be readily removed prior to a needle being associated with the adhesive material.

10. A disposal device for a needle which is adapted for use in a hypodermic syringe, comprising:
    four planar members, each planar member having front and back surfaces, and top edge, bottom edge, and side edge surfaces;
    two of the planar members being flexibly connected together along a side edge surface of each of the two planar members to form a first connected pair of planar members;
    each of the other two planar members being flexibly connected along its top edge surface to the bottom edge surface of one of the planar members of the first connected pair of planar members;
    first means for securing a first portion of the needle to the front surface of one of the planar members of the first connected pair of planar members;
    second means for securing together the front surfaces of the first connected pair of planar members, upon one of planar members of the first connected pair being moved into contact with the other planar member of the first connected pair;
    third means for securing together the front surfaces of the other two planar members upon the movement of one of the other planar members toward one of the other planar members, whereby the first portion of the needle may be first associated with the first securing means, one of planar members of the first connected pair of planar members is moved to engage the second securing means to fixedly sandwich the first portion of the needle between the first connected pair of planar members, and the other two planar members are moved toward each other until one of them engages the third securing means.

11. The disposal device of claim 10, including a fourth means for securing a second portion of the needle, which downwardly depends from the first portion of the needle, to the front surface of one of the other planar members.

12. The disposal device of claim 10, wherein the first securing means comprises an adhesive material disposed on the front surface of one of the planar members of the first connected pair of planar members.

13. The disposal device of claim 11, wherein the fourth securing means comprises an adhesive material disposed on the front surface of one of the other planar members.

14. The disposal device of claim 12, wherein the second securing means is a portion of the same adhesive material that forms the first securing means.

15. The disposal device of claim 10, wherein the third connector means comprises an adhesive material disposed on the first surface of one of the other planar members.

16. The disposal device of claim 13, wherein the third connector means comprises an adhesive material disposed on the first surface of one of the other planar members.

17. The disposal device of claim 16, wherein the fourth securing means is a portion of the same adhesive material that forms the third securing means.

18. The disposal device of claim 12, wherein the second securing means is a connector mechanism having cooperating elements disposed on both planar members of the first connected pair.

19. The disposal device of claim 12, wherein the adhesive material is a layer of foam tape.

20. The disposal device of claim 15, wherein the adhesive material is a layer of foam tape.

21. The disposal device of claim 21, wherein the first securing means includes an indentation formed in at least one front surface of one of the planar members of the first connected pair, the indentation forming a cavity adapted for receipt of the first portion of the needle.

22. The disposal device of claim 21, wherein the second securing means is a connector mechanism having cooperating elements disposed on both planar members of the first connected pair.

23. The disposal device of claim 21, wherein at least a portion of the cavity has an adhesive material therein.

24. The disposal device of claim 10, wherein the back surface of one of the planar members has an adhesive mounting surface adapted to hold a sheath associated with the hypodermic syringe.

25. The disposal device of claim 12, wherein the adhesive material is provided with a removable protective layer, which may be readily removed prior to the first portion of the needle being associated with the adhesive material.

26. A method for preventing accidental contact with a needle of a hypodermic syringe after the needle has been used, comprising the steps of:
   associating the needle with a first planar member by laying the needle upon the first planar member;
   securing the needle to the planar member by the needle contacting an adhesive material disposed upon the first planar member; and
   securing a second planar member to the first planar member with the needle disposed between the two planar members.

27. The method of claim 26, wherein the second planar member is secured to the first planar member by an adhesive material disposed upon the first planar member.

28. The method of claim 26, wherein the second planar member is secured to the first planar member by a connector mechanism having cooperating elements on both of the planar members.

* * * * *

UNITED STATES PATENT AND TRADEMARK OFFICE
CERTIFICATE OF CORRECTION

PATENT NO. : 4,875,896

DATED : October 24, 1989

INVENTOR(S) : Sharon L. Kurtz

It is certified that error appears in the above-identified patent and that said Letters Patent is hereby corrected as shown below:

Col. 9, line 40: The word "sandwiched" should be deleted and the word --sandwich-- inserted.

Signed and Sealed this

Twenty-fifth Day of September, 1990

Attest:

HARRY F. MANBECK, JR.

*Attesting Officer*    *Commissioner of Patents and Trademarks*